United States Patent [19]

Miller et al.

[11] Patent Number: 4,963,623

[45] Date of Patent: Oct. 16, 1990

[54] NATURAL RUBBER LATEX FILM PRODUCTS WITH IMPROVED TEAR RESISTANCE

[75] Inventors: Robert G. Miller, North York; Duncan A. MacKillop; Oskar T. Tankovitz, both of York, all of Canada

[73] Assignee: Ortho Pharmaceutical (Canada) Ltd., Canada

[21] Appl. No.: 295,679

[22] Filed: Jan. 11, 1989

[51] Int. Cl.$^5$ .................... A61F 6/04; C08L 7/00; C08L 25/10

[52] U.S. Cl. .................................. 525/237; 128/844

[58] Field of Search .............. 264/215; 525/237; 128/844; 604/349

[56] References Cited

U.S. PATENT DOCUMENTS

| | | | |
|---|---|---|---|
| 2,266,263 | 12/1941 | Raiche | 264/215 |
| 2,327,638 | 8/1943 | Harrison | 264/215 |
| 2,661,339 | 12/1953 | Sparks et al. | 525/237 |
| 2,747,229 | 5/1956 | Teague | 18/58.5 |
| 2,791,567 | 6/1957 | Lowe et al. | 524/376 |
| 2,809,175 | 10/1957 | Sell | 525/237 |
| 2,880,185 | 3/1959 | Lee | 525/227 |
| 2,896,949 | 7/1959 | Dunker | 525/237 |
| 3,286,011 | 11/1966 | Kavalir et al. | 264/306 |
| 4,356,824 | 11/1982 | Vazquez | 128/350 |
| 4,590,123 | 5/1986 | Hashimoto et al. | 428/316.6 |
| 4,675,347 | 6/1987 | Mochizuki et al. | 523/122 |
| 4,867,968 | 9/1989 | Allen | 523/105 |

FOREIGN PATENT DOCUMENTS

| | | | |
|---|---|---|---|
| 2088389A | of 0000 | United Kingdom . | |
| 984619 | 2/1965 | United Kingdom | 264/215 |

Primary Examiner—Allan M. Lieberman
Attorney, Agent, or Firm—Charles J. Metz

[57] ABSTRACT

Natural rubber latex compounds are modified by the addition of a high styrene content styrene-butadiene copolymer. The films prepared from these modified NR latex compositions exhibit improved tear strength and a good balance of other properties.

4 Claims, No Drawings

NATURAL RUBBER LATEX FILM PRODUCTS WITH IMPROVED TEAR RESISTANCE

The invention relates to natural rubber latex film products which contain a high styrene content styrene-butadiene latex additive. The latex rubber film products of the invention exhibit improved tear resistance.

BACKGROUND OF THE INVENTION

Many prophylactic health care products such as condoms, diaphragms, medical and surgeons' gloves are made from natural rubber ("NR"). NR is available in pure latex form as recovered from the *Hevea Brasiliensis* tree. Thus the preferred manufacturing process is based on the direct conversion of the NR latex into the finished product. This is readily accomplished by dipping shaped-formers into compounded natural rubber latex and removing the water by drying in an oven. Natural Rubber, which is a pure form of stereoregular cis-1,4-polyisoprene, has a very high molecular weight in its native form, and therefore readily forms a continuous film in the dipping/drying process. Also, in order to stabilize the polymeric microstructure, the NR latex is compounded with curatives which cross-link the individual polymer molecules when additional heat is applied.

The cross-linked natural rubber film exhibits a relatively low modulus, giving it good flexibility and extensibility. However, the film also exhibits exceptionally high tensile strength due to strain crystallization reinforcement and a very high level of extension at tensile failure.

The major deficiency of natural rubber is its relatively rapid reversion and degradation on aging, which is initiated by heat, oxygen, ozone, and biological agents. Also as NR films age, they exhibit a tendency to premature failure due to a lowered level of tear resistance.

In the past, there has not been any great urgency to address the improvement in physical properties of natural rubber latex films. However, with the increasing incidence of serious sexually-transmitted diseases, there is significant concern about the integrity and reliability of prophylactic products. The specific objective of the study that led to this invention was to improve the initial and retained tear strength of natural rubber films, which can then be used to produce improved prophylactic condoms, medical and surgical gloves, finger cots, and similar medical products. The invention is also applicable to other products that are made from NR latex films, such as balloons.

SUMMARY OF THE INVENTION

Natural rubber latex compounds are modified by the addition of a high styrene content styrene-butadiene copolymer. The films prepared from these modified NR latex compositions exhibit improved tear strength and a good balance of other properties.

THE PRIOR ART

Published UK patent application No. GB 2 088 389 A, published on June 9, 1982, discloses the use of polyvinyl chloride as an additive to NR latex to improve the tear and puncture resistance of articles made from the latex.

Natural rubber has been blended with synthetic rubbers, including styrene-butadiene copolymer elastomers ("SBR's"), usually in the bulk phase, since the 1930's. The commodity SBR elastomers are based on compositions with about 25% bound styrene content, the remainder of the copolymer being butadiene. Such compositions exhibit good rubbery characteristics with moderate strength. Thus, blends of natural rubber and SBR give useful compositions at low cost which are used in the manufacture of tires and mechanical goods.

Illustrative disclosures of rubber articles made from mixtures of natural rubber and styrene-butadiene copolymers include Hashimoto et al., U.S. Pat. No. 4,590,123 (see, especially, Table 6 in Col. 7), and Vazquez, U.S. Pat. No. 4,356,824 (Col. 11, lines 6–8).

Mochizuki et al., in U.S. Pat. No. 4,675,347, disclose antimicrobial latex compositions containing NR latex and an antimicrobial agent. Among the NR latex compositions disclosed is one containing NR latex and a styrene-butadiene copolymer latex (Col. 10, lines 60 et seq.)

Kavalir et al., in U.S. Pat. No. 3,286,011, disclose rubber gloves that have a non-slip coating on the surface. The non-slip coating may be a mixture of NR latex and a high styrene content styrene-butadiene copolymer latex.

Teague, in U.S. Pat. No. 2,747,229, discloses fabric-lined rubber gloves. The rubber may be a mixture of a styrene-butadiene copolymer and milled raw rubber (col. 5, lines 11–19).

DETAILED DESCRIPTION OF THE INVENTION

The styrene-butadiene latexes that are blended with natural rubber in accordance with the invention are the high styrene content styrene-butadiene ("SB") latexes. Such latexes have greater than 50 weight percent, up to, for example, about 90 weight per cent, and preferably from about 75 to about 85 weight percent, styrene in the copolymer comprising the (SB) latex, the remainder of the copolymer being butadiene.

The addition of the SB latex to the NR latex, in accordance with the invention, does not require any significant modification of the customary production procedures that are followed when making NR articles by the latex dipping process. The two latexes (i.e., the SB and the NR latex) are simply mixed in the appropriate proportions, along with the other additives that are customarily employed in the latex dipping process, and the latex is then used in the customary manner. The SB latex is used in proportions such that the tear strength of the NR latex is improved, without having any adverse effect on other properties. As a general rule, the SB latex will be used in proportions of from about 1 part to about 25 parts, and preferably from about 10 to about 20 parts, by weight, per hundred parts by weight of the NR latex. (These proportions are on a solids basis.)

The invention is useful in the production of prophylactic condoms, medical and surgical gloves, finger cots, prophylactic diaphrams, balloons, and other articles that are made from NR latex films.

The experimental section, below, illustrates the practice of the invention.

EXPERIMENTAL PROCEDURES

Films from blends of natural rubber and an SB copolymer latex were prepared in two separate experimental studies in order to confirm the repeatability of the findings. In each experimental study, a masterbatch compound of natural rubber latex was prepared as a control and as a base for blending with SB copolymer latex.

The film dipping was carried out with a 5 station laboratory dipping machine. The aluminum dipping formers are cylindrical, with a diameter of 5 cm.

The formers were held stationary, and the vessels containing the latex were raised so that the formers were immersed in latex. At the beginning of the dipping sequence, the vessels containing the various latex mixtures are located on a tray mounted directly beneath the formers. The tray is hydraulically lifted at a speed of 40 cm/min, so that the formers are almost completely immersed into the latex.

In the second step, the tray is lowered at a speed of 20 cm/min until the formers are completely out of the latex.

Immediately thereafter, the formers are rotated around their longitudinal axes at a speed of 10 rpm, and they are moved into a horizontal position. While rotating, they are irradiated with a Boekamp 1500 W Quartz heater (Model 1001), at a distance of 20 cm from the formers. Then the dipping and drying sequence is repeated to give a double layer of continuous rubber film. It is standard practice to use this double-dipping procedure in the production of condoms in order to insure the absence of pinholes. When using the invention to produce other NR latex film products, known modifications to the process can be used. For instance, in producing surgical and medical gloves, normally only one latex dip is used, which dip is preceded by a dip in a coagulant (a multi-valent metal salt such as calcium nitrate, calcium chloride, zinc chloride, in a suitable solvent, along with surfactants). The coagulant serves to coalesce the latex particles in a uniform manner. After the latex dip, when a coagulant is used, a leaching step is normally used to remove the coagulant salts prior to the drying/curing step.

The formers are removed from the dipping machine, and placed into a curing oven for 35 minutes at 100° C. After curing, the formers are taken out and cooled for 15 minutes. The film is then dusted with talc, and removed by a simple pulling action.

The physical property data for the NR films are used as controls in comparative testing of the properties of films made from the blends.

A blend of natural rubber latex and SB latex on an 80/20 w/w solids basis was also prepared. This blend and the NR latex control batch were admixed in proportion to give blends with 5, 10, 15, and 20 phr (i.e., parts per hundred parts of NR latex) of styrene-butadiene copolymer component in natural rubber.

Films were prepared by the double-dipping procedure described above. Separate hollow cylindrical formers were dipped simultaneously into separate vessels containing the control and the 5, 10, 15, and 20 phr SB-NR blends. The individual films were dried and then vulcanized in an air convection oven at 100° C. for 35 minutes.

The tear strength and tensile strength on flat films were determined using an Instron 4201 instrument and the procedures of ASTM D624 and D412 respectively. The tensile strength of cylindrical hoop sections were also measured using a rotating spindle holder according to the procedure of ASTM D3492 and D412.

Also some film samples were aged in an air convection oven at 70° C. for one week, and then tested for tear strength.

The films were stripped from the formers after curing, using talc to minimize tack and self-adhesion. Test samples were cut from the rubber films using steel dies and a Carver press.

Physical testing was conducted at room temperature with a minimum of aging time.

TEAR STRENGTH TEST

Tear strength was evaluated using the Instron series IX automated materials testing system, and the ASTM method D624-54. The specimens were cut using die C (90° notch) and the thickness (T) of each specimen at the notch was measured using a micrometer. The gauge length (GL) was 70 mm and the crosshead speed of the Instron was 500 mm/min The tear strength, in N/cm, was calculated from the equation F/T, wherein the maximum load (F) was measured by the Instron. The break elongation was calculated by the equation $(D/GL) \times 100$, wherein the displacement at break (D) was measured by the Instron system.

TENSILE STRENGTH TEST USING DUMBELL SHAPED DIE

According to the ASTM method D412-83, the tensile strength of specimens cut from dumbell die C was obtained using an Instron series IX automated materials testing system. The gauge length (GL) used was 50 mm and the crosshead speed of the Instron was 500 mm/min. The thickness of each specimen, taken from the centre, was measured using a micrometer. The tensile strength, in MPa, was calculated from the equation F/A, wherein the load (F) was measured by the Instron and the area (A) was calculated from the width of die C and the individual thicknesses of the specimens. The percent strain at break was calculated by the equation $(D/GL) \times 100$, wherein the displacement at break (D) is measured by the Instron system.

TENSILE STRENGTH USING RING SPECIMENS

The tensile strength was obtained using the ASTM method D3492-83 and an Instron series IX automated materials testing system. The gauge length or the distance between the centres of the rollers was 30 mm and the crosshead speed of the Instron was 500 mm/min. The minimum thickness (T) of each specimen was measured using a micrometer. The tensile strength, in MPa, was calculated using the equation $F/(2WT)$, wherein the load at break (F) was measured by the Instron and the width (W) of the ring or the die width was 20 mm. The percent strain at break was calculated from the equation $100 \times (2D/C)$ wherein the displacement at break (D) is measured by the Instron system and C is the circumference of the ring specimen.

EXAMPLE 1

The individual NR latex masterbatch and 20 phr blend were prepared in open mixing vessels of about 10 liters volume capacity each. The formulations of the dry ingredients and of the dispersions are given in Table 1 and Table 2, respectively.

In the preparation of the above batches, the ingredients are combined in the order of listing in the tables with constant agitation. The blends of intermediate composition were prepared by admixing the NR latex masterbatch and 20 phr SBR blend in the appropriate proportions, e.g., 468 g of the 20% SB blend diluted with 1404 g of NR latex compound gave the 5% blend.

The blends were transferred to sealable jars and agitated on a roller mixing machine for 48 hours prior to dipping. Films were prepared by dipping hollow cylindrical formers directly into the jars using a special machine built for this purpose, as described above. Entry and withdrawal rates of the formers were closely controlled to give films of uniform thickness. While still mounted on the machine, the films were dried using an infrared lamp and a portable hot air dryer. The formers covered with rubber film were removed from the machine and placed in an air oven at 100° C. for 35 minutes.

The cured films from this experiment were cut into test specimens using the ASTM Die C for tear test specimens and a dumbell die for the specimens for tensile strength measurements. A summary of tear strength and tensile strength data is given in Table 3 and Table 4, respectively.

EXAMPLE 2

The experimental study of Example 1 was repeated using a more recent delivery of Natural Rubber latex and freshly compounded curative dispersions. More than 60 test specimens were prepared and tested in order to conduct a statistical analysis (refer to Tables 6 and 7).

DISCUSSION OF TEST RESULTS

Tear Strength

The films of Example 1 and Example 2 were tested separately for their tear strength, as a measure of tear resistance, using the ASTM procedure D-624-54 and samples cut with Die C. In Example 1, about 25 test specimens were prepared, whereas in Example 2, approximately 60 test specimens were tested.

The data in Table 6 shows that the natural rubber film has a tear strength of about 630 N/cm average. However, there is a considerable range of values indicating that there could be a wide variability in individual film thickness and distribution of surface flaws. There is a considerable variation in average film thickness. This can be attributed in part to surface tension and viscosity effects, particularly in relation to the improvement observed for the blends with the synthetic latex.

When 5 phr of the styrene-butadiene copolymer is added to natural rubber, the latex films exhibit about a 50% increase in tear strength. Similarly, the addition of 10% and 15% SB copolymer provides a further increase in tear strength, with some values double the values for the natural rubber film alone.

It is noted that the consistency of the test results seem to improve with the addition of the synthetic latex. This is likely attributable in part to the presence of additional emulsifiers as well as the physical reinforcement phenomenon. The formulation used for control dipping is basic. In commercial practice, other additives would be included to optimize surface tension and viscosity for optimum wet film deposition.

Also, the incorporation of styrene-butadiene copolymer into the natural rubber matrix will reduce the variations in strength results since the copolymer reduces the initiation of failures caused by intrinsic film flaws.

In general, the tear strength of the blend films increases with the concentration of copolymer and peaks in the range of 10% to 15% concentration. This is consistent with the findings for the addition of other reinforcing polymers to natural rubber. It is interesting to note that the deviation of test results decreases as the concentration of additive increases. Again, this reflects more uniform films, since the deviation of film thickness also decreases, as well as affirms the basic concept that the tendency to tear is flaw dependent, and that the additive makes the film more tear-resistant.

A value for % elongation at break is recorded although this will have questionable validity as portions of the test specimen are subject to differential strain effects and vary in tensile loading. However, since the specimens are all the same size, and mounted in the Instron tester in the same manner, the data can be used in comparative analysis. It is observed in both experiments, and in general for polymeric additives, that with some small addition of copolymer, there is an increase in % elongation. This is likely attributable to the fact that since the copolymer itself is an unsaturated, reactive copolymer, it will utilize some of the available sulfur in intra-particle reaction, and therefore reduce the cross-link density in the bulk matrix, leading to higher extensibility. As the copolymer latex is increased in concentration, the % elongation passes through a maximum, and then begins to decrease again. This can be explained in that there will also be some intermolecular cross-linking between the SB copolymer particles and natural rubber. The particles will act as multinodal cross-link sites, and thus increase the overall cross-link density at higher concentration. Also, there will be some structural dimensional limitation as the natural rubber molecules are limited in their ability to extend.

Tensile Strength

Tensile strength data were determined by two separate tests, i.e. using dumbells as standard for rubber sheet testing, and by a ring test used for condom sections. The actual values of tensile strength in MPa are consistent for both tests. However, the % elongation at break appears to be marginally higher in the dumbell test. With the addition of copolymer, there is a steady increase in tensile strength up to 15% concentration of copolymer.

As observed before for tear, the % elongation at break in tensile testing increases a small percentage with 5% addition, and then steadily decreases with additive concentration. Again, the deviation of test results is improved as the blend concentration increases.

Effect of Thermal Aging

For one set of films, the tear strength was measured on films that were aged in an air convection oven for one week at 70° C. (This is equivalent to 64 months of exposure at room temperature.) The data of Tables 5 and 8 show that the tear strength is significantly reduced by this aging process. For all of the films, i.e. natural rubber plus the four blend compositions, the tear strength is reduced by about one-half from its initial value. There is also a loss of extensibility on air heat aging with % elongation being reduced by 25% for natural rubber and somewhat less for blends as the concentration of SB copolymer increases. In general, the films of blends with 10% to 15% SB copolymer exhibit tear strength after accelerated heat aging equivalent to that for unaged natural rubber film.

COMMERCIAL CONDOMS

One brand of commercial condoms was tested (with 25 specimens) for their tear strength and tensile strength as a standard for current performance and quality and the manufacturing process. The brand tested is non-lubricated, manufactured from quality Natural Rubber Latex.

The data of Tables 9 and 10 summarize the test results. The tear strength of commercial condoms is lower than that for films produced in the laboratory. This is attributed, in part, to the fact that the commercial condoms were about six months old when tested, and it is known that strength properties decrease with time.

4. Potassium laurate solution is 20% w/w of potassium laurate (Pfaltz & Bauer Inc.) in distilled water.

5. The ZDC accelerator is a 50% w/w aqueous dispersion of zinc diethyl dithiocarbamate prepared as ETHAZATE 50D from Uniroyal Chemicals Ltd.

6. Sulfur is a 60% w/w aqueous dispersion supplied by General Latex & Chemicals Ltd.

7. Zinc Oxide (ZnO) is a 40% w/w aqueous dispersion supplied by General Latex & Chemicals Ltd.

8. The Antioxidant is a 40% w/w aqueous dispersion of Goodyear's Wingstay L prepared by General Latex and Chemicals Ltd.

TABLE 1
COMPOUND FORMULATION (DRY BASIS)

| COMPONENT | Control | Blends | | | |
|---|---|---|---|---|---|
| | | PHR | | | |
| NR Latex | 100 | 95 | 90 | 85 | 80 |
| SB Latex | — | 5 | 10 | 15 | 20 |
| Potassium hydroxide | 0.5 | | | | |
| Potassium laurate | 0.5 | | | | |
| Sulfur | 1.25 | | | | |
| ZDC | 1.0 | | | | |
| Zinc oxide | 1.0 | | | | |
| Antioxidant | 1.0 | | | | |

The ingredients are described below, following Table 2.

TABLE 2
WET COMPOUND FORMULATIONS FOR 56% SOLIDS

| | % Solids | NR Masterbatch | 20 phr SBR Blend |
|---|---|---|---|
| NR Latex | 62 | 4839 g | 3870 |
| SB latex | 50 | — | 1200 |
| Potassium hydroxide | 10 | 150 | 150 |
| Potassium laurate | 20 | 75 | 75 |
| Sulfur | 62 | 60 | 60 |
| ZDC | 50 | 60 | 60 |
| Zinc Oxide | 50 | 60 | 60 |
| Antioxidant | 40 | 75 | 75 |
| Water | — | 321 | 90 |
| | | 5640 | 5640 |

MATERIALS

1. Natural rubber latex

The Natural Rubber latex used is a Firestone Hartex 104 high-ammonia natural rubber latex, supplied by General Latex & Chemicals Ltd. Brampton, Ontario. Solids content is 62.0% w/w.

2. Styrene-butadiene latex

The SB latex was DOW SB 816, supplied by DOW Chemical Canada Inc. The polymer composition is 81% styrene: 19% butadiene with glass transition temperature of 45° C.

| Other specification data are as follows: | |
|---|---|
| Solids, % | 49–51 |
| pH | 8.5–9.5 |
| Styrene level | 81% |
| Particle size (Å) | 1850–2550 |
| Surface Tension (Dynes/cm) | 46–60 |
| Tg, °C | 45 |
| Alkali sensitivity | Low |
| Brookfield viscosity (cps) | Below 150 |
| Non-film forming at room temperature | |

3. Potassium hydroxide solution prepared as 10% w/w solution of BDH Chemicals "assured" grade KOH (98% purity) in distilled water.

TABLE 3
TEAR STRENGTH (EXAMPLE 1)

| | Tear Strength (N/cm) | Elongation at break (%) | Specimen Thickness (mm) |
|---|---|---|---|
| All Natural Rubber | 21 Test specimens | | |
| Mean | 714 | 711 | 0.065 |
| Std. Dev. | 187 | 86 | 0.020 |
| Min. | 439 | 611 | 0.040 |
| Max. | 998 | 873 | 0.101 |
| 5% SB/NR Blend | 25 Test specimens | | |
| Mean | 1034 | 826 | 0.059 |
| Std. Dev. | 121 | 49 | 0.016 |
| Min. | 805 | 705 | 0.038 |
| Max. | 1205 | 899 | 0.091 |
| 10% SB/NR Blend | 24 Test specimens | | |
| Mean | 1166 | 745 | 0.047 |
| Std. Dev. | 111 | 32 | 0.009 |
| Min. | 947 | 693 | 0.033 |
| Max. | 1362 | 790 | 0.067 |
| 15% SB/NR Blend | 24 Test specimens | | |
| Mean | 1223 | 698 | 0.052 |
| Std. Dev. | 122 | 31 | 0.014 |
| Min. | 957 | 635 | 0.033 |
| Max. | 1392 | 747 | 0.087 |
| 20% SB/NR Blend | 19 Test specimens | | |
| Mean | 1206 | 618 | 0.047 |
| Std. Dev. | 78 | 26 | 0.011 |
| Min. | 1033 | 563 | 0.031 |
| Max. | 1358 | 666 | 0.066 |

TABLE 4
TENSILE STRENGTH (EXAMPLE 1)
Dumbell Test per ASTM D412

| | Tensile Strength MPa | Elongation at Break (%) |
|---|---|---|
| All Natural Rubber | | |
| Mean | 24.6 | 982 |
| Std. Dev. | 7.2 | 85 |
| Min. | 13.2 | 867 |
| Max. | 33.4 | 1108 |
| 5% SB/NR Blend | | |
| Mean | 27.0 | 940 |
| Std. Dev. | 7.1 | 81 |
| Min. | 15.5 | 774 |
| Max. | 35.8 | 1018 |
| 10% SB/NR Blend | | |
| Mean | 26.9 | 856 |
| Std. Dev. | 3.4 | 82 |
| Min. | 20.2 | 732 |
| Max. | 31.3 | 957 |
| 15% SB/NR Blend | | |
| Mean | 26.4 | 786 |
| Std. Dev. | 2.8 | 57 |
| Min. | 22.2 | 695 |
| Max. | 30.2 | 849 |
| 20% SB/NR Blend | | |
| Mean | 22.9 | 730 |
| Std. Dev. | 0.7 | 73 |
| Min. | 22.0 | 645 |
| Max. | 23.7 | 824 |

TABLE 5
TEAR STRENGTH OF FILMS (EXAMPLE 1)
After Aging 7 Days at 70° C.

| | Tear Strength (N/CM) | Elongation at Break (%) |
|---|---|---|
| Natural Rubber | | |
| Mean | 345 | 592 |
| Std. Dev. | 104 | 39 |
| Range | 170–438 | 524–640 |
| 5% SB/NR | | |
| Mean | 461 | 626 |
| Std. Dev. | 89 | 29 |
| Range | 322–587 | 593–672 |
| 10% SB/NR | | |
| Mean | 681 | 658 |
| Std. Dev. | 132 | 54 |
| Range | 508–915 | 589–763 |
| 15% SB/NR | | |
| Mean | 792 | 653 |
| Std. Dev. | 161 | 96 |
| Range | 597–1033 | 523–772 |
| 20% SB/NR | | |
| Mean | 620 | 506 |
| Std. Dev. | 143 | 125 |
| Range | 416–833 | 308–707 |

TABLE 6
TEAR STRENGTH (EXAMPLE 2)

| | Tear Strength (N/CM) | Elongation at Break % | Thickness (mm) |
|---|---|---|---|
| Natural Rubber | | | |
| Mean | 630 | 771 | .086 |
| Std. Dev. | 104 | 74 | .028 |
| Range | 370–803 | 590–898 | .035–.154 |
| 5% SB/NR | | | |
| Mean | 909 | 831 | .067 |
| Std. Dev. | 109 | 55 | .028 |
| Range | 650–1129 | 696–951 | .036–.163 |
| 10% SB/NR | | | |
| Mean | 976 | 817 | .067 |
| Std. Dev. | 121 | 46 | .024 |
| Range | 661–1295 | 682–925 | .034–.121 |
| 15% SB/NR | | | |
| Mean | 1030 | 679 | .060 |
| Std. Dev. | 99 | 37 | .022 |
| Range | 722–1294 | 551–742 | .029–.098 |

TABLE 7
TENSILE STRENGTH (EXAMPLE 2)

| | Tensile Strength (MPa) | Elongation at Break (%) |
|---|---|---|
| Natural Rubber | | |
| Mean | 23.8 | 823 |
| Std. Dev. | 3.2 | 28 |
| Range | 17.7–32.8 | 720–852 |
| 5% SB/NR | | |
| Mean | 27.2 | 836 |
| Std. Dev. | 3.2 | 21 |
| Range | 18.7–34.8 | 788–866 |
| 10% SB/NR | | |
| Mean | 25.7 | 780 |
| Std. Dev. | 2.3 | 33 |
| Range | 20.4–29.1 | 702–832 |
| 15% SB/NR | | |
| Mean | 24.6 | 720 |
| Std. Dev. | 2.1 | 20 |
| Range | 20.9–30.5 | 671–750 |

TABLE 8
TEAR STRENGTH OF FILMS (EXAMPLE 2)
After Aging 7 Days at 70° C.

| | Tear Strength (N/CM) | Elongation at Break (%) |
|---|---|---|
| Natural Rubber | | |
| Mean | 415 | 568 |
| Std. Dev. | 64 | 31 |
| Range | 318–493 | 515–598 |
| 5% SB/NR | | |
| Mean | 567 | 569 |
| Std. Dev. | 74 | 33 |
| Range | 403–637 | 495–599 |
| 10% SB/NR | | |
| Mean | 683 | 550 |
| Std. Dev. | 112 | 80 |
| Range | 520–814 | 433–665 |
| 15% SB/NR | | |
| Mean | 621 | 438 |
| Std. Dev. | 61 | 41 |
| Range | 502–700 | 356–482 |

TABLE 9
TEAR STRENGTH OF COMMERCIAL CONDOMS
ASTM D624 DIE C

| Brand | Tear Strength (N/CM) | Range |
|---|---|---|
| A-regular | 529 | 369–598 |
| A-lubricated | 531 | 426–656 |
| B-regular | 474 | 408–572 |
| B-lubricated | 564 | 515–620 |
| C-regular | 605 | 438–809 |
| C-lubricated | 543 | 415–674 |

TABLE 10
COMMERCIAL CONDOMS

| | Tensile Strength (MPa) | Elongation at Break (%) |
|---|---|---|
| Mean | 23.4 | 788 |
| Std. Dev. | 5.2 | 43 |
| Range | 11.5–33.9 | 677–856 |

| | Tear Strength (N/CM) | Elongation at break (%) |
|---|---|---|
| Mean | 492 | 567 |
| Std. Dev. | 185 | 82 |
| Range | 309–981 | 445–770 |

What is claimed is:

1. A prophylactic condom comprising a natural rubber film comprising cured natural rubber and a styrene-butadiene copolymer, wherein said copolymer contains greater than 50 weight percent polymerized styrene, the remainder being polymerized butadiene, and wherein said copolymer is present in an amount within the range of from about 1 to 25 parts, by weight, per 100 parts by weight of natural rubber.

2. The prophylactic condom of claim 1 wherein said styrene-butadiene copolymer contains from about 75 to about 85 weight percent polymerized styrene.

3. The prophylactic condom of claim 1 wherein the styrene-butadiene copolymer is present in an amount of from about 10 to about 20 parts, by weight, per 100 parts by weight of natural rubber.

4. The prophylactic condom of claim 2 wherein the styrene-butadiene copolymer is present in an amount of from about 10 to about 20 parts, by weight, per 100 parts by weight of natural rubber.

* * * * *